US012758964B2

(12) United States Patent
Keller

(10) Patent No.: US 12,758,964 B2
(45) Date of Patent: Oct. 13, 2026

(54) PIPETTE TIP WITH TWO POSITIVE ANGLE STEPS

(71) Applicant: TECAN TRADING AG, Männedorf (CH)

(72) Inventor: Michael Keller, Bauma (CH)

(73) Assignee: TECAN TRADING AG, Maennedorf (CH)

( * ) Notice: Subject to any disclaimer, the term of this patent is extended or adjusted under 35 U.S.C. 154(b) by 1077 days.

(21) Appl. No.: 17/839,258

(22) Filed: Jun. 13, 2022

(65) Prior Publication Data

US 2023/0064079 A1 Mar. 2, 2023

(30) Foreign Application Priority Data

Aug. 30, 2021 (EP) .................................... 21193715

(51) Int. Cl.
*B01L 3/00* (2006.01)
*B01L 3/02* (2006.01)
*C12M 1/26* (2006.01)

(52) U.S. Cl.
CPC ........... *B01L 3/0275* (2013.01); *B01L 3/0293* (2013.01); *B01L 3/5635* (2013.01); *C12M 33/04* (2013.01);
(Continued)

(58) Field of Classification Search
CPC .... B01L 3/0275; B01L 3/0293; B01L 3/5635; B01L 2200/025; B01L 2200/026;
(Continued)

(56) References Cited

U.S. PATENT DOCUMENTS

| | | | |
|---|---|---|---|
| 5,223,225 | A | 6/1993 | Gautsch |
| 2018/0221863 | A1 | 8/2018 | Cadotte, Jr. et al. |
| 2019/0344258 | A1 | 11/2019 | Motadel et al. |

FOREIGN PATENT DOCUMENTS

| | | | |
|---|---|---|---|
| EP | 3272851 | B1 | 1/2018 |
| EP | 3492926 | B1 | 6/2019 |

(Continued)

OTHER PUBLICATIONS

Wikipedia "Capillary Action" (Year: 2020).*
(Continued)

*Primary Examiner* — Charles Capozzi
*Assistant Examiner* — Michael Stanley Gzybowski
(74) *Attorney, Agent, or Firm* — MH2 Technology Law Group LLP

(57) ABSTRACT

A pipette includes an end section, a first section, a second section and a third section aligned along a central axis of the pipette tip. The end section comprises an orifice for aspirating and dispensing a fluid. A first kink is formed in an inner surface of the pipette tip between the first section and the second section, such that an angle between the inner surface of the first section and the central axis is smaller than an angle between the inner surface of the second section and the central axis. A second kink is formed in the inner surface of the pipette tip between the second section and the third section, such that the angle between the inner surface of the second section and the central axis is smaller than an angle between the inner surface of the third section and the central axis.

13 Claims, 4 Drawing Sheets

(52) U.S. Cl.
CPC ... *B01L 2200/025* (2013.01); *B01L 2200/026* (2013.01); *B01L 2200/0615* (2013.01); *B01L 2200/0689* (2013.01); *B01L 2300/0858* (2013.01)

(58) Field of Classification Search
CPC ..... B01L 2200/0615; B01L 2200/0689; B01L 2300/0858; C12M 33/04
See application file for complete search history.

(56) References Cited

FOREIGN PATENT DOCUMENTS

| | | | | | |
|---|---|---|---|---|---|
| EP | 2606977 | B1 | | 7/2019 | |
| EP | 3575000 | A1 | * | 12/2019 | ............ B01L 3/0279 |
| WO | 2014/179256 | A1 | | 11/2014 | |
| WO | 2016/028998 | A1 | | 2/2016 | |

OTHER PUBLICATIONS

EP3575000A1—English translation (Year: 2019).*
Chinese Office Action and Search Report issued in corresponding Chinese Patent Application No. 202210674000.4, dated Jun. 23, 2025, with English language translation, 10 pages.

* cited by examiner

PIPETTE TIP WITH TWO POSITIVE ANGLE STEPS

CROSS-REFERENCE TO RELATED APPLICATION(S)

This application claims priority to European Application No. EP 21 193 715.6, filed Aug. 30, 2021, the entire contents of which is incorporated herein by reference.

FIELD OF THE INVENTION

The invention relates to a pipette tip, for example for a laboratory automation device.

BACKGROUND OF THE INVENTION

Laboratory automation devices are used for automating tasks of a laboratory assistant, which, for example, tests a patient for specific diseases. Usually, a sample of the patient's blood, urine, stool, etc. is taken and analyzed by means of a bio-chemical procedure. Such a procedure consists in various operations like adding substances, incubating, separating, etc. and a measurement process which quantitatively or qualitatively measures the amount or presence of a substance indicating the specific disease.

The samples are usually aspirated and dispensed with disposable pipette tips, which can be plugged onto nozzles of a handheld pipette or of a movable head of the laboratory automation devices. A handheld pipette may be actuated mechanically by the operator or it is actuated electronically. The geometric form of the pipette tips is crucial for an exact aspiration and dispensing process. Sometimes it is desirable that the amount of sample liquid aspirated and dispensed is controllable as exact as possible, in particular, when small volumes are aspirated and dispensed.

Several types of pipette tips have been designed subject to different needs with respect to the aspiration and dispensing process.

EP 3 272 851 B1 shows a pipette tip, which has a first cylindrical section with an orifice, a tapered section and a second cylindrical section with larger diameter than the first cylindrical section.

US 2019 0344 258 A1 shows a pipette tip, which has a conical section with an orifice and a cylindrical section.

EP 2 606 977 B1 shows several pipette tips composed of cylindrical and conical sections.

EP 3 492 926 B1 shows a pipette tip composed of conical sections with different opening angles.

DESCRIPTION OF THE INVENTION

It is an objective of the invention to provide a pipette tip with which small amounts of liquid can be aspirated and dispensed exactly. A further objective of the invention is to increase the accuracy and precision of the amount of liquid being aspirated or dispensed with a laboratory automation device.

This objective is achieved by the subject-matter of claim 1. Further exemplary embodiments are evident from the dependent claims and the following description.

The invention relates to a pipette tip. In general, a pipette tip may be an elongated body with a cavity inside into which a liquid or other fluid can be aspirated or dispensed therefrom by changing a pressure in the cavity. Usually, pipette tips are composed of several sections with different inner diameters, which can be cylindrical and conical.

The pipette tip may be designed to be used with a laboratory automation device, for example may have an attachment section to be plugged onto a movable head of the laboratory automation device. However, the pipette tip also may be a part of a hand-held device.

According to an embodiment of the invention, the pipette tip comprises an end section, a first section, a second section and a third section aligned along a central axis of the pipette tip, wherein the end section comprises an orifice for aspirating and dispensing a fluid, in particular a liquid, emulsion or suspension. The pipette tip may be substantially rotationally symmetric with respect to the central axis. In particular, the end section, the first section, the second section and the third section, as well as the cylindrical section mentioned below may be rotationally symmetric.

According to an embodiment of the invention, a first kink is formed in an inner surface of the pipette tip between the first section and the second section, such that an angle between the inner surface of the first section and the central axis is smaller than an angle between the inner surface of the second section and the central axis. Additionally, a second kink is formed in the inner surface of the pipette tip between the second section and the third section, such that an angle between the inner surface of the second section and the central axis is smaller than an angle between the inner surface of the third section and the central axis.

Between the kinks, the inner surface of the pipette tip may be continuous and/or may have no or nearly no curvature. A kink also may be characterized by a region, where the curvature of the inner surface is rather high and/or where the radius of curvature is small. The curvature of the inner surface at the kinks is substantially higher (such as at least 10 times higher) as the curvature of the inner surface between the kinks.

Each of the first and second kink and also the kinks mentioned below may circumvent the central axis and/or may have a circular shape with circle center at the central axis.

The angle of a surface with respect to the central axis may be defined as the angle between a line inside the surface and the central axis, wherein the line is the cross-section of the surface with a plane going through the central axis.

In other words, the angles of the inner surfaces of the first, second and third section, which inner surfaces may be rotational symmetric with respect to the central axis, increase in this order. In such a way, two kinks are formed, which may be seen as positive kinks, i.e. they are protruding towards the inside of the pipette tip. When the fluid level passes one of these kinks during aspiration or dispensing, the border of the surface of the fluid stays or sticks at the kink due to capillary forces, even when the pressure inside the tip changes. There may be a range of volumes, which can be aspirated or dispensed, all of which have a fluid level at the respective kink. This effect can be used to better control the amount of fluid inside the pipette tip. In particular at the kinks, the amount of fluid aspirated and dispensed can be controlled with pressure changes rather accurately, since the border of the surface of the fluid does not move and is not subjected to uncontrollable movements caused by capillary forces.

A corresponding effect may take place at negative kinks, i.e. kinks that protrude away from the inside of the pipette tip. There, the liquid level may increase and decrease without a pressure change resulting in uncontrollable ranges of volume. Depending on the liquid and the tip material, a combination of a positive and a negative kink may be favorable.

The pipette tip as described herein solely has positive kinks in an end part comprising the first, second and third section. Thus, at lower volumes, the control of the aspirated and dispensed volume is improved.

According to an embodiment of the invention, an angle between the inner surface of the first section and the inner surface of the second section, i.e. the angle at the first kink, is larger than 1° and/or is smaller than 5°. Additionally and/or optionally, an angle between the inner surface of the second section and the inner surface of the third section, i.e. the angle at the second kink, is larger than 1° and/or is smaller than 5°. Experiments and tests have been shown that an angle at a kink should be larger than 1°. Otherwise, the above mentioned effect of staying or sticking of the fluid surface becomes too weak. Also, for angles of more than 5°, the effect usually becomes too strong to be beneficial.

It has to be noted that a real angle size can deviate by up to 10% of the angle size provided here, i.e. the angle of 1° mentioned above can be a real, measured angle from 0.9° to 1.1°. The same applies to the angles mentioned below.

According to an embodiment of the invention, the angle between the inner surface of the first section and the central axis is larger than 2° and/or smaller than 5°, in particular 3°. The angle between the inner surface of the second section and the central axis may be larger than 3° and/or smaller than 9°, in particular 5°. The angle between the inner surface of the third section and the central axis may be larger than 4° and/or smaller than 13°, in particular 6.5°.

Further tests showed that these absolute angles (compared to the relative angles between the sections) resulted in well controllable volumes within the first, second and third section of the pipette tip.

According to an embodiment of the invention, the position of the first kink between the first section and the second section is chosen, such that an inner volume of the pipette tip between the orifice and the first kink is between 0.3 μl and 0.6 μl, in particular 0.5 μl. The first pipetted volume may be fixed to 0.5 μl. As a further example, the first pipetted volume may be about 1.0 μl.

The position of the second kink between the second section and the third section is chosen, such that an inner volume of the pipette tip between the orifice and the second kink is between 0.8 μl and 1.2 μl, in particular 1.0 μl. The second pipetted volume may be fixed to 1.0 μl. The second pipetted volume be 2 μl or even 5 μl. Here also a range between 4.5 μl to 5.5 μl may be chosen.

As mentioned above, at the kinks, the volume of the fluid in pipette can be controlled very accurately. When positioning the kinks at positions, where the pipette has a specific inner volume, the aspiration and dispensing of an amount of the fluid having the specific inner volume can be controlled more accurately.

According to an embodiment of the invention, a length of the third section along the central axis is chosen, such that an inner volume of the pipette tip between the orifice and the length is at least a nominal volume of the pipette tip, such that at least 5 μl, or at least 10 μl. The third section may be used for aspirating much higher amount of fluid than the first and second section. The length of the third section also may be chosen such that an inner volume of the pipette tip between the orifice and the length is at least 5 times an inner volume of the pipette tip between the orifice and the second kink.

It also may be that a cylindrical section following the third section is present and that the nominal volume of the pipette is defined including the inner volume of the cylindrical section. In the case one defined volume is desired, the third section may be skipped and then the second section and/or a cylindrical section following the second section may be designed to allow bigger volumes.

As already mentioned, the inner surfaces of the pipette tip may have no or nearly no curvature between the kinks. Such surfaces may be defined by frustum of cones and cylinders.

According to an embodiment of the invention, the inner surface of the first section is conical, the inner surface of the second section is conical and/or the inner surface of the third section is conical. In this context, "conical" means frusto-conical in a mathematical sense.

The end section of the pipette tip may have a conical inner surface and the inner surface between the end section and the first section of the pipette tip may have a further kink.

According to an embodiment of the invention, a further kink is formed in the inner surface of the pipette tip between the end section and the first section.

According to an embodiment of the invention, an angle between the inner surface of the end section and the inner surface of the first section is larger than 2° and/or is smaller than 5°.

According to an embodiment of the invention, the inner surface of the end section is cylindrical. The inner surface of the end section may have the same radius as the orifice, which may be defined by a border of the inner surface.

It has to be noted that an inner surface with a cylindrical shape may have an angle up to 0.5° with respect to the central axis due to reasons of manufacturing. For example, if the pipette tip is made by injection moulding, it may be necessary that the inner surface deviates a bit from pure cylindrical in the mathematical sense, such that a mould tool can be removed from the pipette tip after moulding.

According to an embodiment of the invention, a common outer surface of the first section, the second section and the third section and optionally the end section is conical. An angle of the outer surface with respect to the central axis may be the angle of the third section with respect to the central axis. Thus, a wall thickness of the pipette tip may increase in the end section, the first section and the second section.

According to an embodiment of the invention, the pipette tip comprises an attachment section for attaching the pipette tip to a nozzle of a laboratory automation device for changing a pressure inside the pipette tip. The nozzle may be a part of a moving head of the laboratory automation device. The attachment section is aligned along the central axis of the pipette tip following the third section and optionally a cylindrical section (see below). The attachment section may have a larger inner diameter than the third section and/or the cylindrical section. An angle between the inner surface of the attachment section and the central axis may be smaller than an angle between the inner surface of the third section and the central axis.

The attachment section also may have longitudinal ribs at an outside of the pipette tip for reinforcing the wall of the pipette tip there.

According to an embodiment of the invention, the attachment section is formed, such that a further pipette tip of the same shape is partially insertable into the attachment section to at least the third section, for stacking the further pipette tip and the pipette tip.

According to an embodiment of the invention, the pipette tip comprises a cylindrical section between the attachment section and the third section aligned along a central axis of the pipette tip and following the third section. The cylindrical section may have a length, which is larger than a length of the pipette tip between the orifice and the beginning of the cylindrical section. It even may be that the length of the cylindrical section is at least two times or at least five times larger than the of the pipette tip between the orifice and the beginning of the cylindrical section.

When the first and second kink (and also the further kink between the end section and the first section) are considered as positive kinks, where the angle increases, a negative kink is formed between the third section and the cylindrical section, where the angle decreases with increasing distance from the orifice.

According to an embodiment of the invention, the pipette tip comprises a filter section, which may be a part of the attachment section. The filter section is aligned along a central axis of the pipette tip and may follow the third section and/or the cylindrical section. The inner surface of the filter section may comprise ribs extending radially around the central axis. The filter section may have a larger inner diameter than the third section and/or the cylindrical section.

It has to be noted that the pipette tip may comprise more than three sections and/or more than two optimized volumes. Also solely one optimized volume is possible.

These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

The reference symbols used in the drawings, and their meanings, are listed in summary form in the list of reference symbols. In principle, identical parts are provided with the same reference symbols in the figures.

DETAILED DESCRIPTION OF EXEMPLARY EMBODIMENTS

Figure 1:
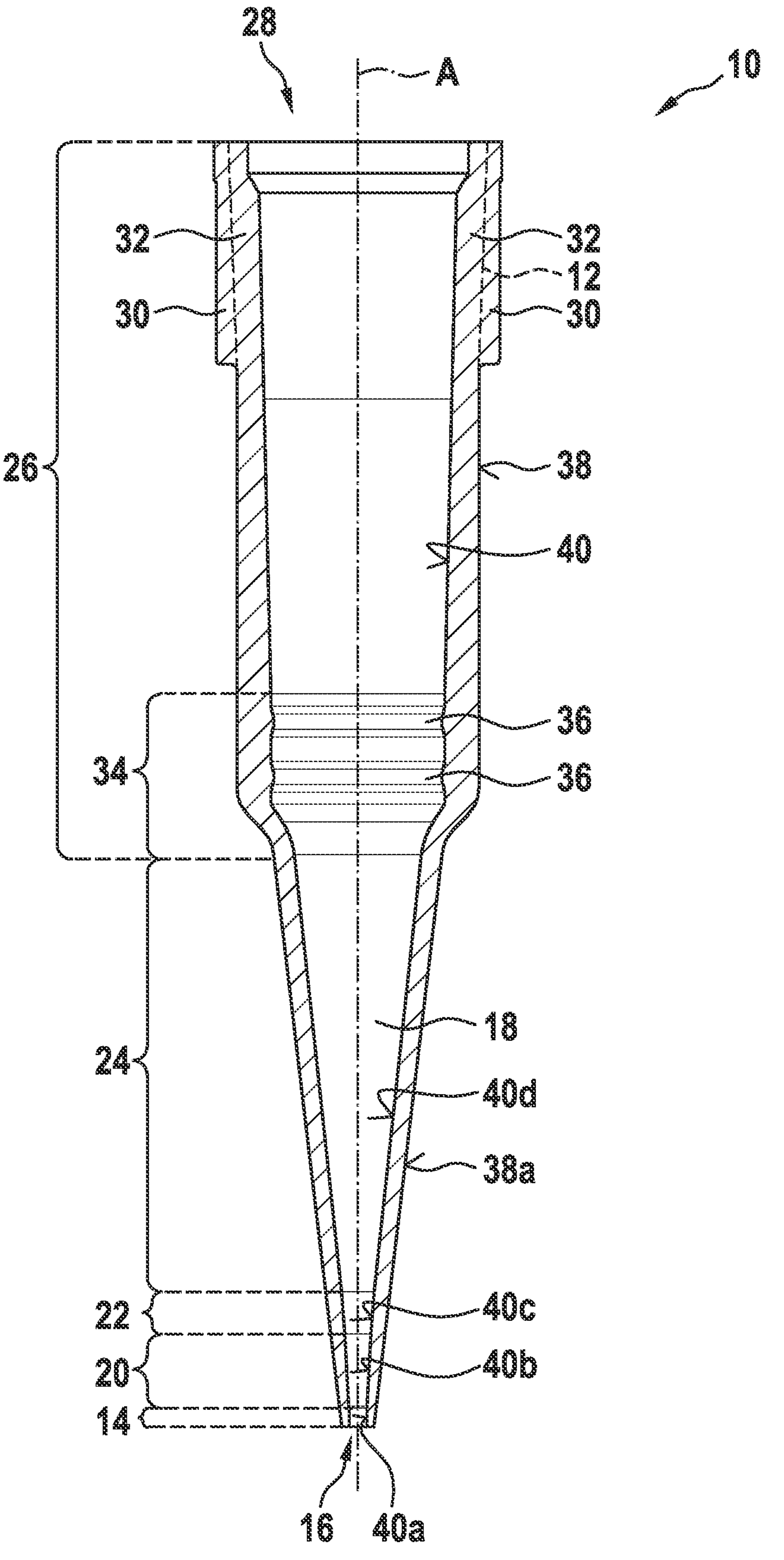
FIG. 1 shows a cross sectional view of a pipette tip according to an embodiment of the invention.

FIG. 1 shows a pipette tip 10, which can be used with a manual pipette or laboratory automation device. The pipette tip 10 comprises a substantially rotational symmetric body 12 with respect to a central axis A.

The pipette tip 10 can be divided into several sections of different geometric forms.

An end section 14 comprises an orifice 16 for aspirating a fluid into an inner cavity 18 of the pipette tip 10. The orifice 16, which may be circular, may have a diameter between 0.3 mm and 1.0 mm and/or the outer end of the pipette tip 10 may have a diameter of about 0.8 mm. The end section 14 may have a length of about 0.5 mm.

Along the axis A, a first section 20, second section 22 and third section 24 follows the end section 14 in this order. All of these sections as well as the end section are rotational symmetric with respect to the central axis A and/or have a circular cross-section orthogonal to the central axis A. Also, slightly oval cross-sections are possible. The first section 20 has a length of about 2.0 mm, the second section 22 of about 1.2 mm and the third section of about 12.4 mm. Here and in the following, the lengths are dependent on desired volumes for the respective sections in dependence of the diameters of the respective sections.

The end section 14, the first section 20, the second section 22 and the third section 24 are rotational symmetric with respect to the axis A. Again, slightly oval cross-sections are possible.

The pipette tip 10 furthermore comprises an attachment section 26 with an opening 28 opposite to the orifice 16. The attachment section 26 is designed for being connected to a nozzle of the a laboratory automation device or handheld pipette, which nozzle may be plugged into the opening 28. At an outer end, the attachment section 26 comprises ribs 30, which extend substantially parallel to the central axis A and which are provided on an outside of the pipette tip 10 and its body 12. In FIG. 1, a cross-section through a pair of opposite ribs 30 is shown. The thickness of a wall 32 of the attachment section 26 besides the ribs 30 is like the thickness of the wall 32 in a region, where no ribs 30 are present any more, i.e. towards the orifice 16.

The attachment section 26 has a length of about 19 mm. Except the ribs, the attachment section 26 is rotational symmetric with respect to the axis A.

The attachment section 26 is connected to the third section 24. At an end connected to the third section 24, the attachment section 26 comprises a filter section 34. The filter section 34 is designed for receiving a cylindrical filter piece and/or has inner ribs 36, which circumvent the central axis A on an inside of the pipette tip 10. The filter section 34 has a length of about 4 mm. The filter section 34 is rotational symmetric with respect to the axis A.

The pipette tip 10 and its body 12 may be made of plastics material. The plastic material may be conductive e. g. by graphite additives or may be non-conductive e. g. polypropylene. The pipette tip 10 may be manufactured by injection moulding, wherein an outer surface 38 is formed by an outer mould tool and an inner surface 40 is formed by an inner mould tool.

The inner surface 40*a* of the end section 14 is cylindrical and has the same diameter like the orifice 16. The inner surface 40*b* of the first section 20, the inner surface 40*c* of the second section 22 and the inner surface 40*d* of the third section 24 is conical. The terms "cylindrical" and "conical" relate to the shell surfaces of the respective body. There also may be pipette tips without a cylindrical end section. Such tips may have a very short end section, which may be the lower end of the first section, which provides the orifice.

It may be that the end of the inner surface 40*d* of the third section, which goes over into the inner surface of the attachment section 26, opens up shaped like a trumpet, i.e. with continuously increasing surface angle with respect to the central axis A.

An inner diameter of the first section 20, second section 22 and third section 24 is continuously increasing with increasing distance from the orifice 16. The angle with respect to the central axis A may be constant within a section. The angle increases from section to section with growing distance to the end section.

Figure 2:
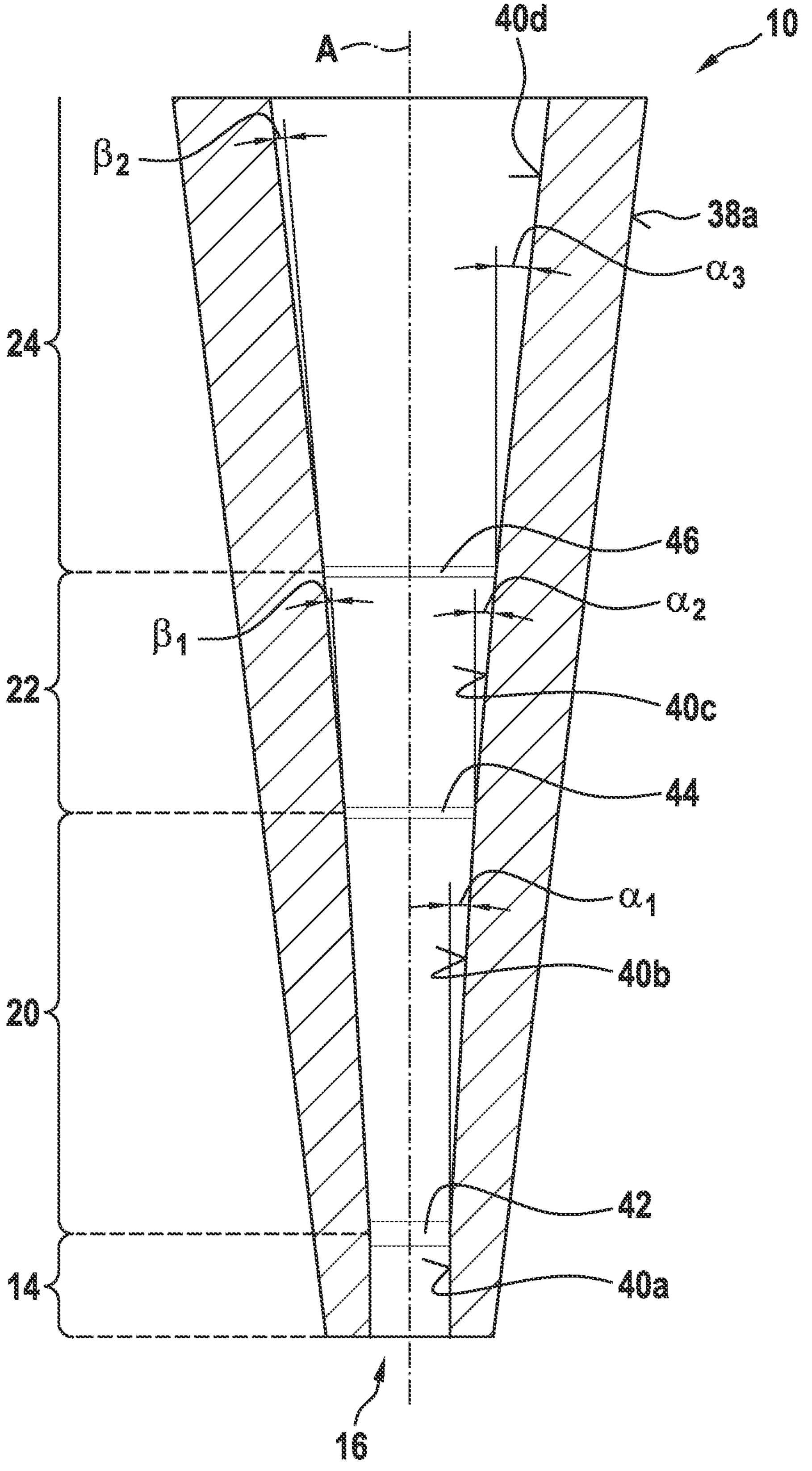
FIG. 2 shows an enlarged view of an end of the pipette tip of FIG. 1.

FIG. 2 shows an enlarged view of the sections 14, 20, 22, 24 of the pipette tip 10. It can be seen that a kink 42 is formed between the inner surface 40*a* of the end section 14 and the inner surface 40*b* of the first section 20, that a kink 44 is formed between the inner surface 40*b* of the first section 20 and the inner surface 40*c* of the second section 22 and that a kink 46 is formed between the inner surface 40*c* of the second section 22 and the inner surface 40*d* of the third section 24.

As described above, the accuracy and precision of the amount of fluid to be aspirated and dispensed, when the pipette tip is filled up to the respective kink 44, 46, can be increased. The positions of the kinks 44, 46 can be chosen, such that the accuracy at specific volumes is increased.

In the embodiment shown in FIGS. 1 and 2, the position of the kink 44 is chosen, such that an inner volume of the pipette tip 10 between the orifice 16 and the kink 44 is about 0.5 μl. Also, the position of the second kink 46 is chosen, such that an inner volume of the pipette tip 10 between the orifice 16 and the second kink 46 is about 1.0 μl.

The third section 24 may be substantially longer than the first section 20 and the second section 22 and/or may have a substantially larger inner volume. The length of the third section 24 along the central axis A is chosen, such that an inner volume of the pipette tip 10 between the orifice 16 and the length is at least a nominal volume of the pipette tip 10, such that as more than 5 μl, for example 10 μl.

The kinks 42, 44, 46 are formed by a sudden step in the angle between the inner surface 40 of the pipette tip and the axis A. Each of the angles $\alpha_1$, $\alpha_2$, $\alpha_3$, which are present between the central axis A and the surfaces 40*b*, 40*c*, 40*d*, is higher than the previous one, i.e. the inner surface 40 of the pipette tip 10 opens up at every kink 42, 44, 46. The kink 42 solely may be present in the case of a cylindrical end section 14.

The angle $\alpha_1$ between the inner surface 40*b* of the first section 20 and the central axis A is smaller than the angle $\alpha_2$ between the inner surface 40*c* of the second section 22 and the central axis A. The angle $\alpha_2$ between the inner surface 40*c* of the second section 22 and the central axis A is smaller than the angle $\alpha_3$ between the inner surface 40*d* of the third section 24 and the central axis A.

As described above, the following ranges of angles have been shown to achieve the beneficial effects of increasing the controllability of aspirating and dispensing and the accuracy at the volumes defined by the kinks 44, 46.

The angle $\alpha_1$ between the inner surface 40*b* of the first section 20 and the central axis A may be larger than 2° and/or smaller than 5°, such as 3°. The angle $\alpha_2$ between the inner surface 40*c* of the second section 22 and the central axis A may be larger than 3° and/or smaller than 9°, such as 5°. The angle $\alpha_3$ between the inner surface 40*d* of the third section 24 and the central axis A may be larger than 4° and/or smaller than 13°, such as 6.5°.

The angle $\beta_1$ between the inner surface 40*b* of the first section 20 and the inner surface 40*c* of the second section 22 is the difference of the angles $\alpha_2$ and $\alpha_1$. The angle $\beta_1$ is larger than 1° and/or is smaller than 5°. The angle $\beta_2$ between the inner surface 40*c* of the second section 22 and the inner surface 40*d* of the third section 24 is the difference of the angles $\alpha_3$ and az. The angle $\beta_2$ is larger than 1° and/or is smaller than 5°.

It is not necessary that the outer surface 38 of the pipette tip 10 also has kinks. In the present embodiment, a common outer surface 38*a* of the end section 14, the first section 20, the second section 22 and the third section 24 is conical.

Figure 3:
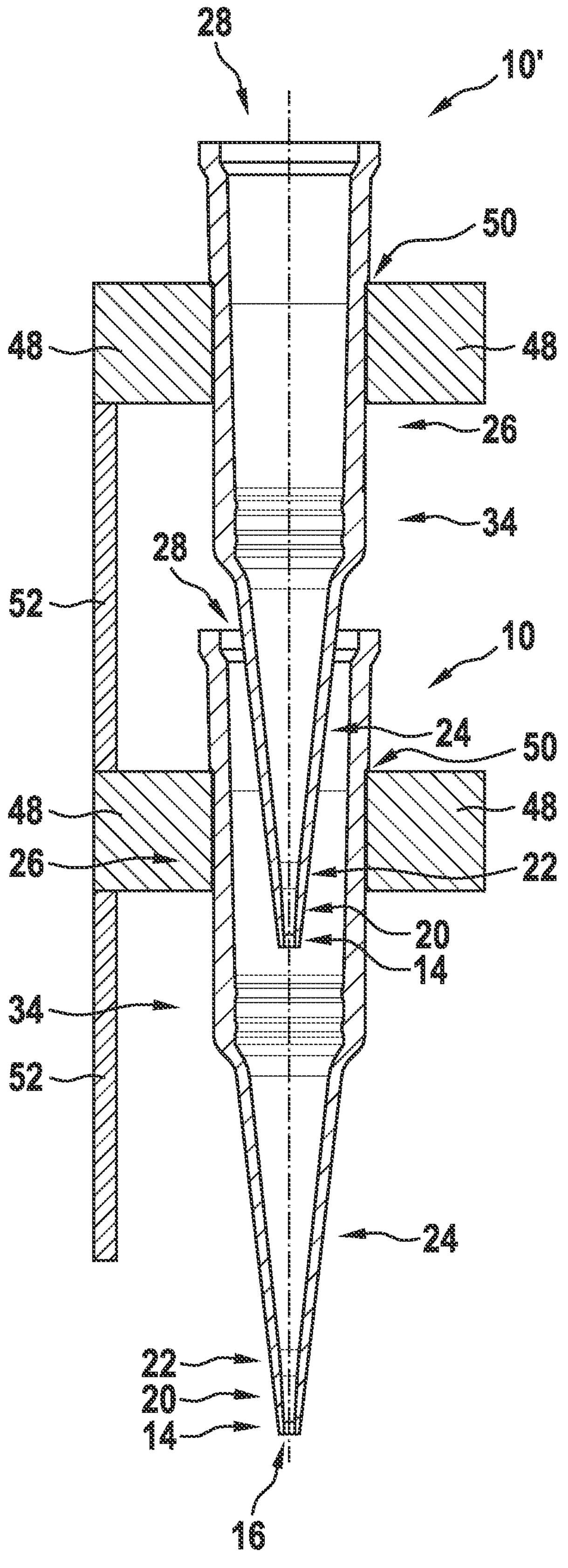
FIG. 3 shows a cross sectional view of two pipette tips according to FIG. 1 stacked into each other.

FIG. 3 shows the pipette tip 10 of FIGS. 1 and 2 and a further pipette tip 10' of the same design. It is shown that the attachment section 26 is formed, such that the further pipette tip 10' is partially insertable into the attachment section 26 to at least the third section, for stacking the further pipette tip 10' and the pipette tip 10. The pipette tips 10, 10' hang in a tray 48 with holes 50. The holes 50 have a smaller diameter than the outside diameter of the ribs 30 and a larger diameter than the outside diameter of the coupling section without ribs 30. The trays 48 are kept at a distance by spacers 52 so that the space for stacking is optimally used.

The third section 24, which has the largest outer diameter of the sections 14, 20, 22, 24, has an outer diameter smaller than the inner diameter of the attachment section 26 at the opening 28. Furthermore, the length of the attachment section 26 (without the optional filter section 34) is at least 80% of the overall length of the sections 14, 20, 22, 24.

Figure 4:
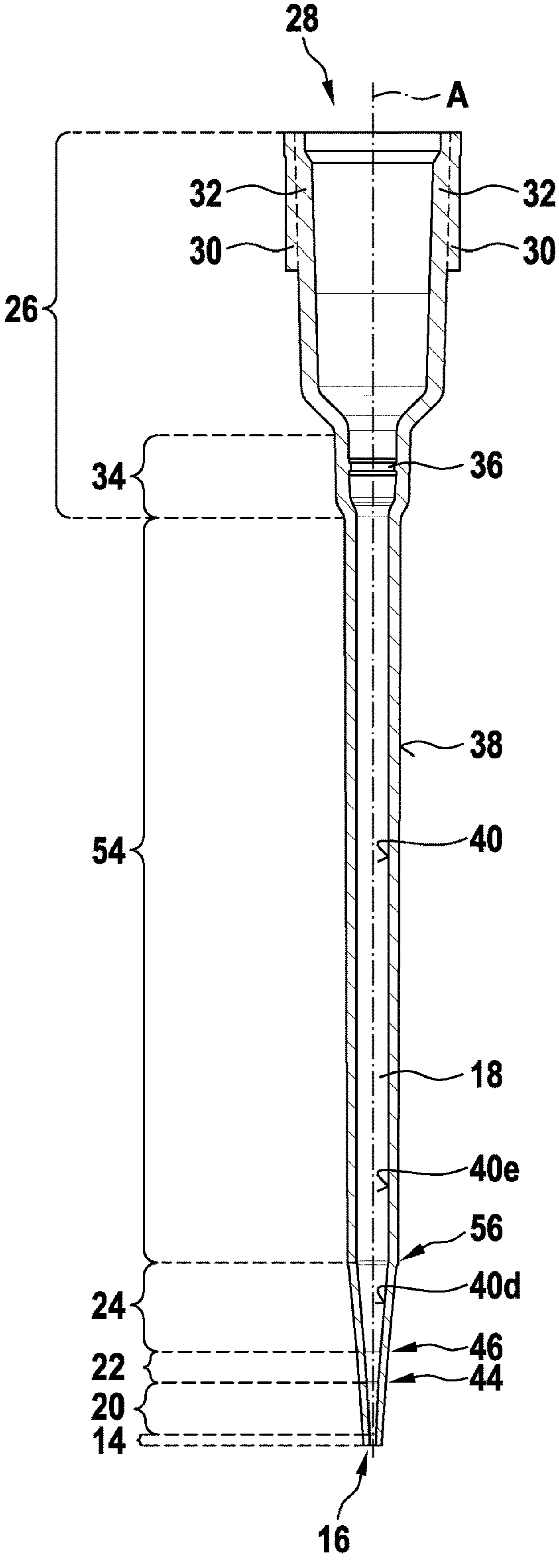
FIG. 4 shows a cross sectional view of a pipette tip according to a further embodiment of the invention.

FIG. 4 shows a pipette tip 10, which additionally comprises a cylindrical section 54 between the third section 24 and the attachment section 26. With the cylindrical section 54, the nominal volume of the pipette 10 can be substantially increased. The cylindrical section 54 is longer than the pipette tip 10 between the orifice 16 and the cylindrical section 54, i.e. longer than the sections 14, 20, 22, 24.

The other parts of the pipette tip 10 of FIG. 4 can be designed as the corresponding parts of pipette tip 10 of FIGS. 1 to 3. In particular, the pipette tip 10 of FIG. 4 also comprises the kinks 44, 46, which increase the accuracy in aspirating and dispensing as described above.

The pipette tip 10 of FIG. 4 comprises a kink 56 between the inner surface 40*d* of the third section 24 and the inner surface 40*e* of the cylindrical section 54, which however protrudes away from the central axis A contrary to the kinks 42, 44, 46.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A pipette tip comprising:

an end section, a first section, a second section and a third section aligned along a central axis of the pipette tip;

wherein the end section comprises an orifice for aspirating and dispensing a fluid, the first section is adjacent to the end section, the second section adjacent to the first section, and the third section adjacent to the second section;

wherein a first kink is formed in an inner surface of the pipette tip between the first section and the second section, such that an angle ($\alpha 1$) between the inner surface of the first section and the central axis is smaller than an angle ($\alpha 2$) between the inner surface of the second section and the central axis;

wherein a second kink is formed in the inner surface of the pipette tip between the second section and the third section, such that the angle ($\alpha 2$) between the inner surface of the second section and the central axis is smaller than an angle ($\alpha 3$) between the inner surface of the third section and the central axis, wherein the first kink and the second kink are formed, such that when a fluid level passes one of the first kink and the second kink during aspiration or dispensing of the fluid, a border of the surface of the fluid stays or sticks at the first kink and the second kink due to capillary forces, even when a pressure inside the pipette tip changes;

wherein an angle between the inner surface of the first section and the inner surface of the second section is larger than 10° and is smaller than 5°, and wherein an angle between the inner surface of the second section and the inner surface of the third section is larger than 10° and is smaller than 5°, wherein a position of the first kink is arranged, such that an inner volume of the pipette tip between the orifice and the first kink is between 0.3 μl and 0.6 μl.

2. The pipette tip of claim 1, wherein the angle ($\alpha$1) between the inner surface of the first section and the central axis is larger than 2° and smaller than 5°;

wherein the angle ($\alpha$2) between the inner surface of the second section and the central axis is larger than 3° and smaller than 9°;

wherein the angle ($\alpha$3) between the inner surface of the third section and the central axis is larger than 4° and smaller than 13°.

3. The pipette tip of claim 1, wherein a position of the second kink is arranged, such that an inner volume of the pipette tip between the orifice and the second kink is between 0.8 μl and 1.2 μl.

4. The pipette tip of claim 1, wherein a length of the third section along the central axis is arranged, such that an inner volume of the pipette tip between the orifice and the length is at least a nominal volume of the pipette tip.

5. The pipette tip of claim 1, wherein the inner surface of the first section is conical;

wherein the inner surface of the second section is conical;

wherein the inner surface of the third section is conical.

6. The pipette tip of claim 1, wherein a further kink is formed in the inner surface of the pipette tip between the end section and the first section.

7. The pipette tip of claim 1, wherein an angle between the inner surface of the end section and the inner surface of the first section is larger than 2° and is smaller than 5°.

8. The pipette tip of claim 1, wherein the inner surface of the end section is cylindrical.

9. The pipette tip of claim 1, wherein a common outer surface of the first section, the second section and the third section is conical.

10. The pipette tip of claim 1, wherein the pipette tip comprises a cylindrical section aligned along the central axis of the pipette tip following the third section;

wherein the cylindrical section is longer than the pipette tip between the orifice and the cylindrical section.

11. The pipette tip of claim 1, wherein the pipette tip comprises a filter section aligned along the central axis of the pipette tip, the filter section following the third section;

wherein the inner surface of the filter section comprises ribs extending radially around the central axis.

12. The pipette tip of claim 1, wherein the pipette tip comprises an attachment section for attaching the pipette tip to a nozzle of a laboratory automation device for changing a pressure inside the pipette tip;

wherein the attachment section is aligned along the central axis of the pipette tip following the third section.

13. The pipette tip of claim 12, wherein the attachment section is formed, such that a further pipette tip is partially insertable into the attachment section to at least the third section, for stacking the further pipette tip and the pipette tip.

* * * * *